United States Patent
Kawanabe et al.

[11] Patent Number: 5,488,874
[45] Date of Patent: Feb. 6, 1996

[54] LIQUID ASPIRATING METHOD

[75] Inventors: Junichi Kawanabe; Masaaki Takeda; Hitomi Katagi; Yuko Kato, all of Mitaka, Japan; Gregory A. Bielarczyk, Lombard; Rosie L. Magee, Oak Park, both of Ill.

[73] Assignee: Abbott Laboratories, Abbott Park, Ill.

[21] Appl. No.: 211,802

[22] PCT Filed: Oct. 15, 1992

[86] PCT No.: PCT/JP92/01344

§ 371 Date: Jul. 5, 1994

§ 102(e) Date: Jul. 5, 1994

[87] PCT Pub. No.: WO93/08476

PCT Pub. Date: Apr. 29, 1993

[30] Foreign Application Priority Data

Oct. 18, 1991 [JP] Japan .................................. 3-271482

[51] Int. Cl.⁶ .................................................. G01N 1/00
[52] U.S. Cl. ................................................. 73/863.01
[58] Field of Search ............................ 73/863.01, 863.02, 73/864.23–864.25, 864.13, 864.16–864.18, 54.07, 54.08, 54.13; 422/100

[56] References Cited

U.S. PATENT DOCUMENTS

| | | | |
|---|---|---|---|
| 4,083,363 | 4/1978 | Philpot, Jr. | 73/54.07 |
| 4,675,301 | 6/1987 | Charneski et al. | 73/863.01 |
| 4,893,515 | 1/1990 | Uchida | 73/864.34 |

FOREIGN PATENT DOCUMENTS

| | | |
|---|---|---|
| 56-164957 | 12/1981 | Japan . |
| 56-203985 | 12/1981 | Japan . |
| 59-80661 | 4/1984 | Japan . |
| 61-54427 | 3/1986 | Japan . |

Primary Examiner—Robert Raevis
Attorney, Agent, or Firm—Mark C. Bach

[57] ABSTRACT

The present invention aims to shorten an aspiration time, when aspirating a red blood cell component of a liquid sample having high viscosity. When aspirating the red blood cell component of a blood sample through a nozzle tip, a piston is pulled at its maximum to produce a maximum aspirating force, and starts aspiration. When a pressure in an aspirating system becomes equal to a predetermined value $\alpha$, the piston is returned to a position in which only a necessary aspiration volume of the liquid sample can be aspirated. Since the maximum aspirating force of the pump is utilized during the aspiration, the aspirating operation can be carried out more quickly.

1 Claim, 11 Drawing Sheets

FIG. 8 RED BLOOD CELL DILUTING PROCESS

LIQUID ASPIRATING METHOD

DETAILED DESCRIPTION OF THE INVENTION

Industrial Field of Utilization

The present invention relates to a liquid aspirating method and more particularly to a liquid aspirating method which is used in a pipetting apparatus for pipetting a high-viscosity liquid such as a red blood cell component or the like.

PRIOR ART

Figure 10:
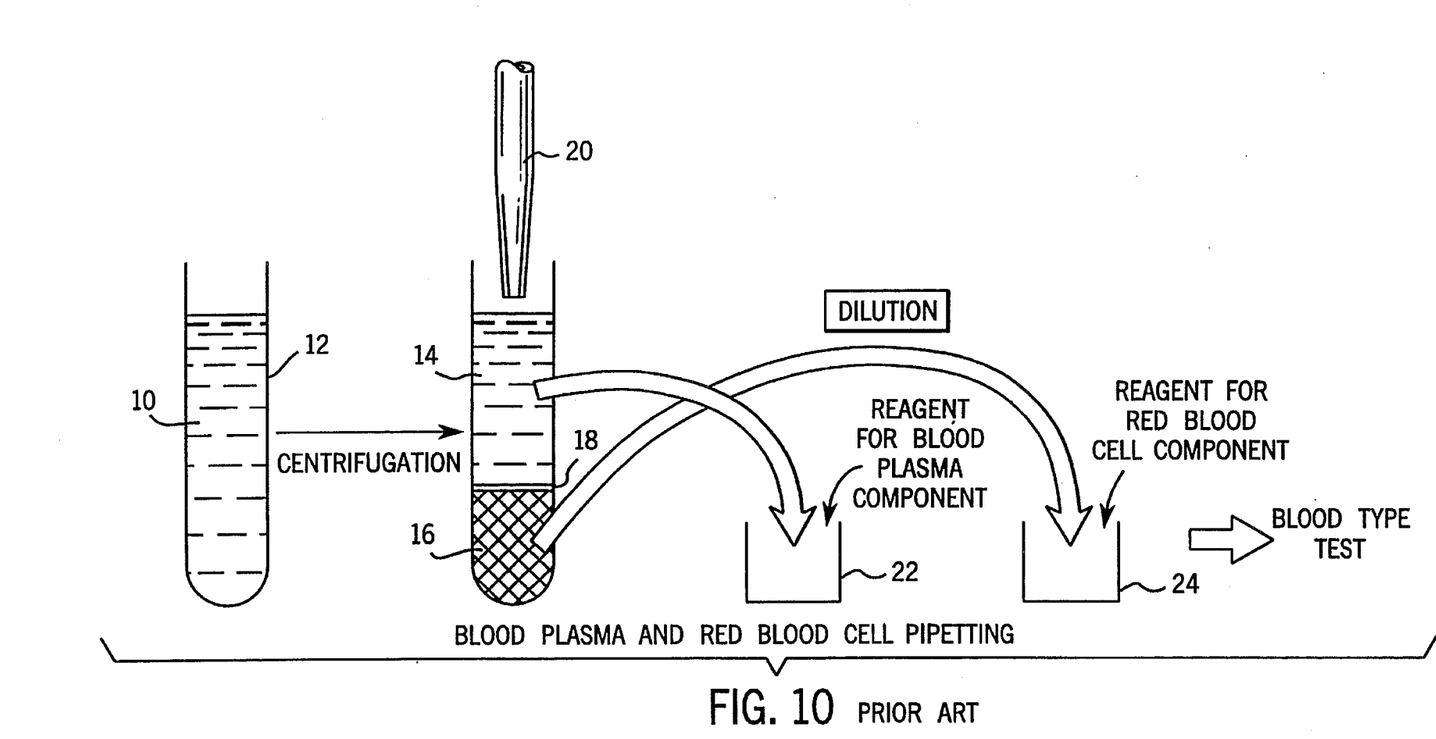
FIG. 10 is an explanatory view showing an operation of pipetting the blood plasma and the red blood cells as a preprocess for a blood type test.

Various kinds of tests are conducted on a blood sample collected from a human body. For example, in a blood type test, as shown in FIG. 10, a collected blood sample 10 is put into a test tube 12 and is then separated into a blood plasma component 14 and a red blood cell component 16 by centrifuging it or leaving it as it is. Practically, a small quantity of white blood cell component 18 appears between the blood plasma component 14 and the red blood cell component 16. Since the white blood cell component 18 is not relevant to the following description of the present invention, it is not shown in other drawings.

A blood sample pipetting method which is carried out in a conventional pipetting apparatus generally comprises two processes, including a process of pipetting blood plasma and a process of pipetting red blood cells. In the blood plasma pipetting process, the blood plasma component 14 is aspirated through a nozzle tip 20, and then dispensed into a plurality of other recipient containers 22 in a predetermined volume, respectively. In the red blood cell pipetting process, the red blood cell component 16 is aspirated through the nozzle tip 20, and then transferred to a diluting container (not shown) to be mixed with a diluent. Thereafter, the diluted red blood cell component 16 is aspirated again through the nozzle tip 20 and then dispensed into each of a plurality of other recipient containers 24, respectively in a predetermined volume.

Blood type testing reagents (i.e., a reagent for the blood plasma component and a reagent for the red blood cell component) are introduced into the recipient containers 22, 24, respectively.

Then, these recipient containers 22, 24 are conveyed to an agglutination testing apparatus, where agglutination of the samples in the containers 22, 24 are measured optically or visually. On the basis of the results of the measurements, A type, B type, 0 type or AB type, or Rh type, or the like is determined.

Figure 11:
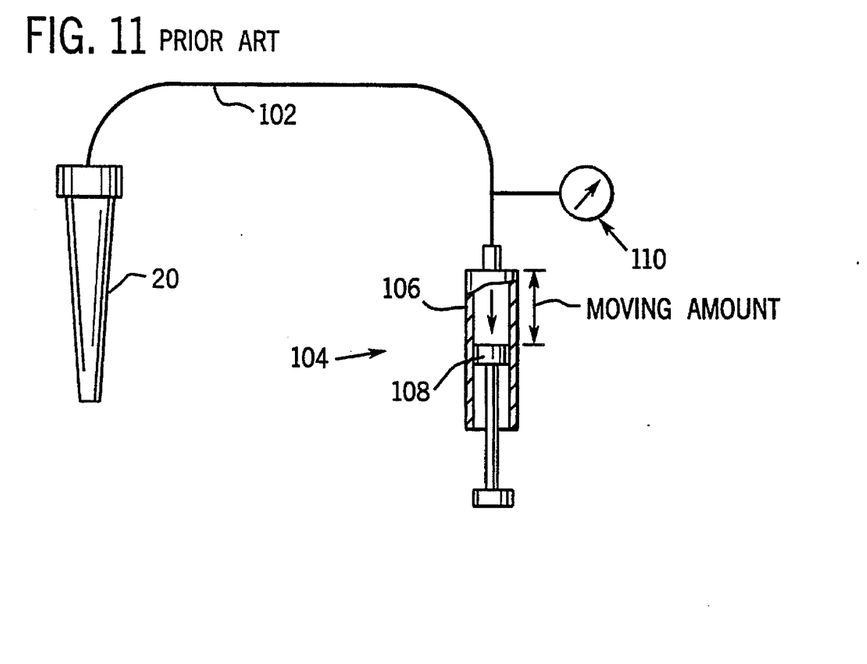
FIG. 11 is a schematic view showing an aspirating portion of the pipetting apparatus.

FIG. 11 shows schematically a construction of an aspirating section of a conventional pipetting apparatus. To the nozzle tip 20, a pump 104 for producing an aspirating force and a dispensing force is connected via an air hose 102. The pump 104 includes a syringe 106 and a piston 108. By moving the piston 108 upwardly and downwardly, an inside volume of the syringe 106 varies, and this inside volume variation is transmitted to the nozzle tip 20 via the air hose 102 to generate the aspirating force or the dispensing force. The aspirating volume (or dispensing volume) is determined, depending on a moving amount of the piston 108.

Figure 12:
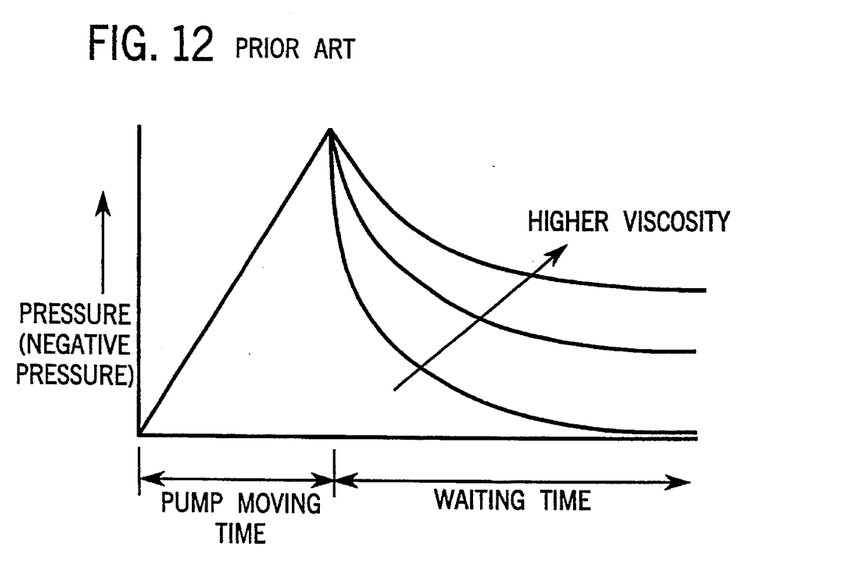
FIG. 12 is a characteristic graph showing a general relationship between an elapsed time and an aspirating pressure in the aspirating system when aspirating each of liquid samples having different viscosities.

FIG. 12 shows a general relationship between a time elapsed after starting of movement of the pump 104 and a pressure in an aspirating system detected by a pressure sensor 110.

As shown in FIG. 12, in case where the piston 108 has been moved by a predetermined distance within a pump moving time, characteristics of the pressure change depending on the viscosity of the blood sample to be aspirated. When a predetermined aspirating pressure is produced by the pump 104 to aspirate a predetermined volume of the blood sample, a waiting time becomes longer in accordance with increase of the viscosity of the liquid sample. As well known, the red blood cell component is a high-viscosity liquid (or a gel-like substance). So, when aspirating the red blood cell component through the nozzle tip 20, the aspiration volume does not follow the moving amount of the piston 108 quickly. After a predetermined time lapses after the aspiration starts, a predetermined volume of the liquid sample is aspirated. The predetermined time, i.e. the waiting time becomes longer with the increase of the liquid viscosity.

PROBLEMS TO BE SOLVED BY THE INVENTION

As aforementioned, when aspirating a predetermined volume of the liquid sample in the conventional pipetting apparatus, the moving amount of the piston 108 is determined in accordance with the predetermined volume of the liquid sample. The pressure sensor 110 monitors completion of the aspiration of the predetermined volume of the liquid sample into the nozzle tip 20.

Consequently, when aspirating the red blood cell component having high viscosity, it is impossible to aspirate it quickly. As a result, it is impossible to improve the pipetting ability per unit time of the pipetting apparatus.

For example, a liquid having a viscosity of about 100 cp requires a waiting time about ten times that required in the water having a viscosity of about 1 cp. Specifically, it takes five, to ten seconds for aspirating the liquid of about 100 cp at one time. Therefore, in an automatic pipetting apparatus for pipetting a large volume of the liquid sample, the pipetting ability per unit time in the aforementioned case is one-tenths of the water.

The present invention has been made in view of above problems. It is therefore an object of the present invention to provide a liquid aspirating method which enables to shorten a required aspirating time as much as possible, when aspirating a liquid sample, especially a blood sample having high viscosity, in an aspirating apparatus for aspirating the liquid sample.

MEANS FOR SOLVING THE PROBLEMS

According to the present invention, the aforementioned object is achieved by a liquid aspirating method in an aspirating apparatus including a nozzle tip for aspirating a liquid sample, an aspiration pump having a piston and a syringe connected with said nozzle tip, and a pressure sensor for monitoring a pressure in an aspirating system, in which an aspirating volume of said liquid sample into the nozzle tip is determined on the basis of a moving amount of said piston, wherein said method comprising the steps of:

(a) setting the moving amount of said piston to such a degree that can aspirate a liquid sample more than a necessary aspirating volume into the nozzle tip, when starting aspiration; and (b) returning the moving amount of the piston to such a degree that can aspirate only the necessary aspirating volume into the nozzle tip, when the pressure in the aspirating system becomes equal to a predetermined pressure, thereby aspirating only the necessary volume of the liquid sample into the nozzle tip.

OPERATION OF THE INVENTION

In the aforementioned features, a moving amount of the piston is first set to a degree that can aspirate a liquid sample more than a necessary aspiration volume. Thereafter, the moving amount of the piston is returned to the degree that can aspirate only the necessary aspiration volume when the pressure of the aspirating system becomes equal to a predetermined pressure. Therefore, it is possible to set an initial aspirating pressure to a high value, especially in case of aspiration of a high-viscosity liquid. As a result, an aspiration time is shortened as a whole, and quick aspiration can be achieved. That is, since the moving amount of the piston is set to a degree that can aspirate the liquid sample more than the necessary aspiration volume, a volume more than the necessary volume is aspirated, if the piston is kept as it is. However, in the present invention, the piston is returned just before an actual aspiration volume exceeds the necessary volume, therefore only the necessary aspiration volume can be aspirated, finally.

Figure 13:
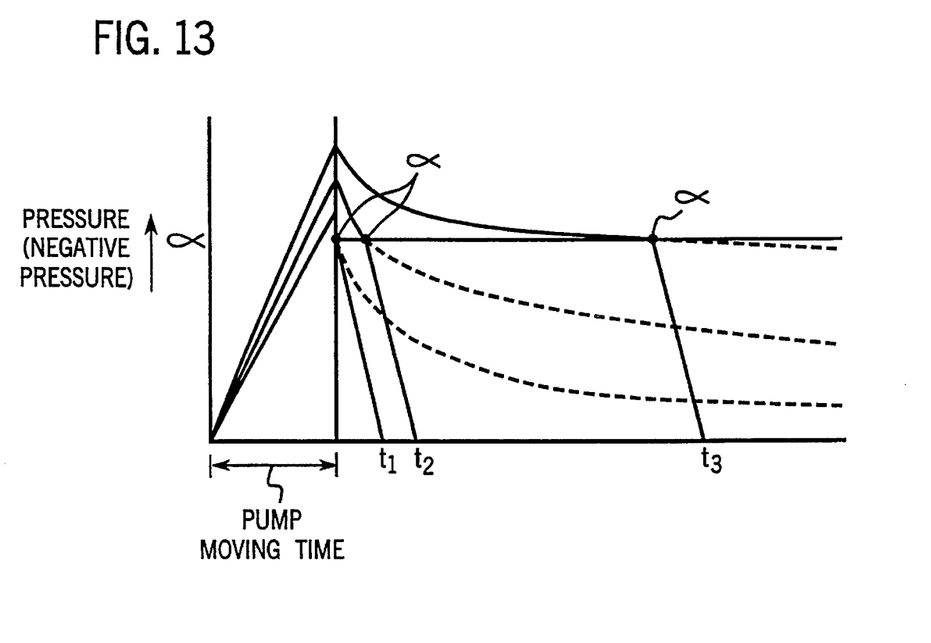
FIG. 13 is a characteristic graph showing the relationship between the elapsed time and the aspiration pressure when the aspirating method of the present invention is used.

This operation will now be described with reference to FIG. 13. FIG. 13 shows the relationship between an elapsed time and a pressure in an aspiration system during the aspiration. According to the present invention, the piston is moved downwardly so as to aspirate the liquid sample more than the necessary aspiration volume during a pump moving time. So, at a time when the pump moving time elapses, the aspiration force becomes greater than that by a conventional method. For example, a maximum aspirating force of the pump is produced. When the pressure in the aspirating system becomes equal to a predetermined pressure $\alpha$, the moving amount of the piston is returned to the degree in which only the necessary aspiration volume of the liquid sample can be aspirated, whereby the aspiration force is immediately reduced. Finally, only the necessary aspiration volume of the liquid sample is aspirated into the nozzle tip.

In FIG. 13, since the moving amount of the piston is determined to be a predetermined value (maximum) for each of liquid samples having different respective viscosities, the inclination of the characteristic curve showing a pressure during the pump moving time somewhat differs depending on the viscosity of the liquid sample to be aspirated. In FIG. 1B, $t_1$, $t_2$, $t_3$ designate times of termination of the aspiration for the liquid samples having different viscosities, respectively.

EMBODIMENTS

Embodiments of the present invention will now be described with reference to the accompanying drawings.

Figure 1:
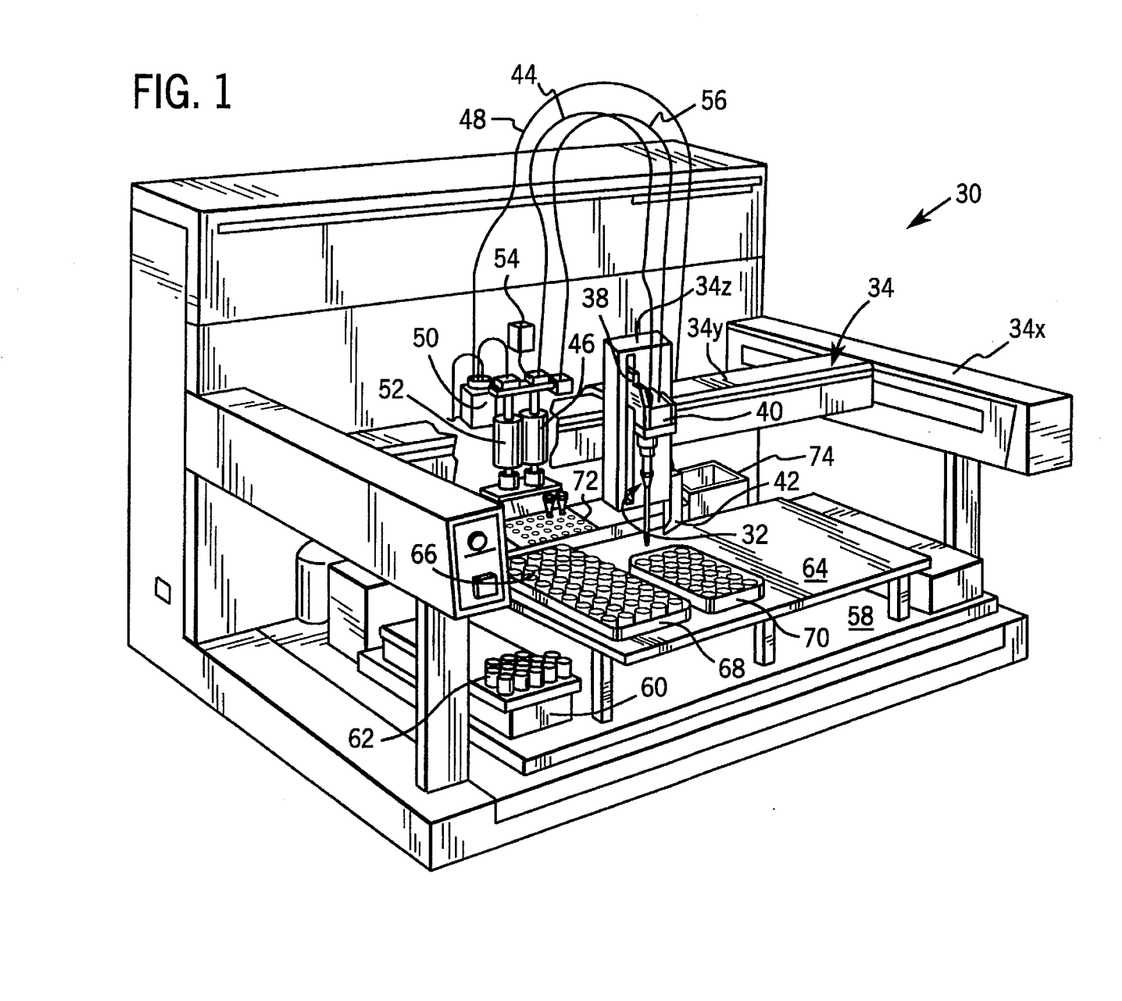
FIG. 1 is a schematic view showing an embodiment of a pipetting apparatus in which an aspirating method of the present invention is used.

FIG. 1 shows a perspective view showing schematically a pipetting apparatus 30 in which an aspirating method according to the present invention is used.

In this embodiment, the apparatus 30 pipettes the blood plasma component and the red blood cell component obtained by centrifugation to perform a preprocess for blood type test.

In the roughly central portion of FIG. 1, there is shown a nozzle 32 for aspirating a blood sample, which is held by an XYZ robot 34 so as to be movable three-dimensionally.

Figure 2:
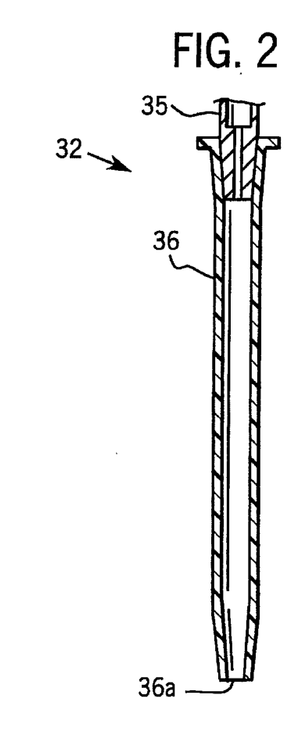
FIG. 2 is a cross-sectional view showing a main part of a nozzle.

FIG. 2 shows a cross sectional view of a main part of the nozzle 32. The nozzle 32 is composed of a nozzle base 35, and a disposable tip 36 (hereinafter called "tip") serving as a nozzle tip. Thus, the pipetting apparatus in the embodiment of the present invention uses a disposable type nozzle tip. A distal end of the nozzle base 35 is forced into an upper opening of the nozzle tip 36 and is fitted therein. Thus, the nozzle tip 36 is fixed firmly to the nozzle base 35. The nozzle tip 36 has at its lower end a smaller orifice 36a from which the blood sample is aspirated and dispensed. The nozzle tip 36 may be made of a hard plastic material or the like, and the nozzle base 35 may be made of a metal.

In FIG. 1, the XYZ robot 34 is composed of an X drive portion 34x, an Y drive portion 34y and a Z drive portion 34z. On the Z drive portion 34z, an elevator 38 equipped with the nozzle 32 is mounted so as to be vertically movable. The elevator 38 has a limit switch 40 serving as a jamming sensor or the like.

The limit switch 40 detects an external force imparted upwardly to the nozzle 32 and having a value greater than a predetermined force.

Onto the Z drive portion 34z, a diluent pipette 42 for dispensing a diluent is fixedly mounted. An air hose 44 is connected at one end thereof to the nozzle 32 and at the other end thereof to a syringe 46 serving as a pump for causing aspirating and dispensing actions. A diluent hose 48 is connected at one end thereof to the diluent pipette 42 and at the other end thereof to a syringe 52 via an electromagnetic valve 50.

Between the syringe 46 and the nozzle 32, a pressure sensor 54 for measuring an internal pressure of the air hose 44 is connected. A signal from the limit switch 40 is fed to the apparatus via a cable 56.

On a test tube rack 60 placed on a pipetting table 58, a plurality of test tubes 62 each containing a blood sample which has been already subjected to a centrifugation treatment are held uprightly. Each test tube 62, as shown in FIG. 10, contains the blood sample in which the blood plasma component and the red blood cell component are separated in an upper portion and a lower portion of the test tube 62, respectively. On a horizontal table 64 mounted on the pipetting table 58, a dilution tray 68 equipped with a plurality of diluting containers 66, and a microplate 70 are placed. On the microplate 70, there are provided a plurality of wells each serving as a recipient container for containing the blood plasma component or the diluted red blood cell component. After all of the blood samples have been pipetted, the microplate 70 is conveyed to an apparatus for blood type test, by which an agglutination test, for example, is made optically. Further, the agglutination test may be made visually.

In the apparatus of the present invention, the nozzle tip is a disposable type. A plurality of new nozzle tips are prepared on a nozzle tip stand 72, and the nozzle tip already used is exchanged with a new one. There is also provided a nozzle scrap tray 74.

Therefore, in the apparatus according to the present invention, it is possible to aspirate the blood plasma component or the red blood cell component through the nozzle tip 36 of the nozzle 32 and then transfer it into other recipient container. This apparatus may also be applied to purposes other than pipetting of the blood sample. Various kinds of applications are possible.

Figure 3:
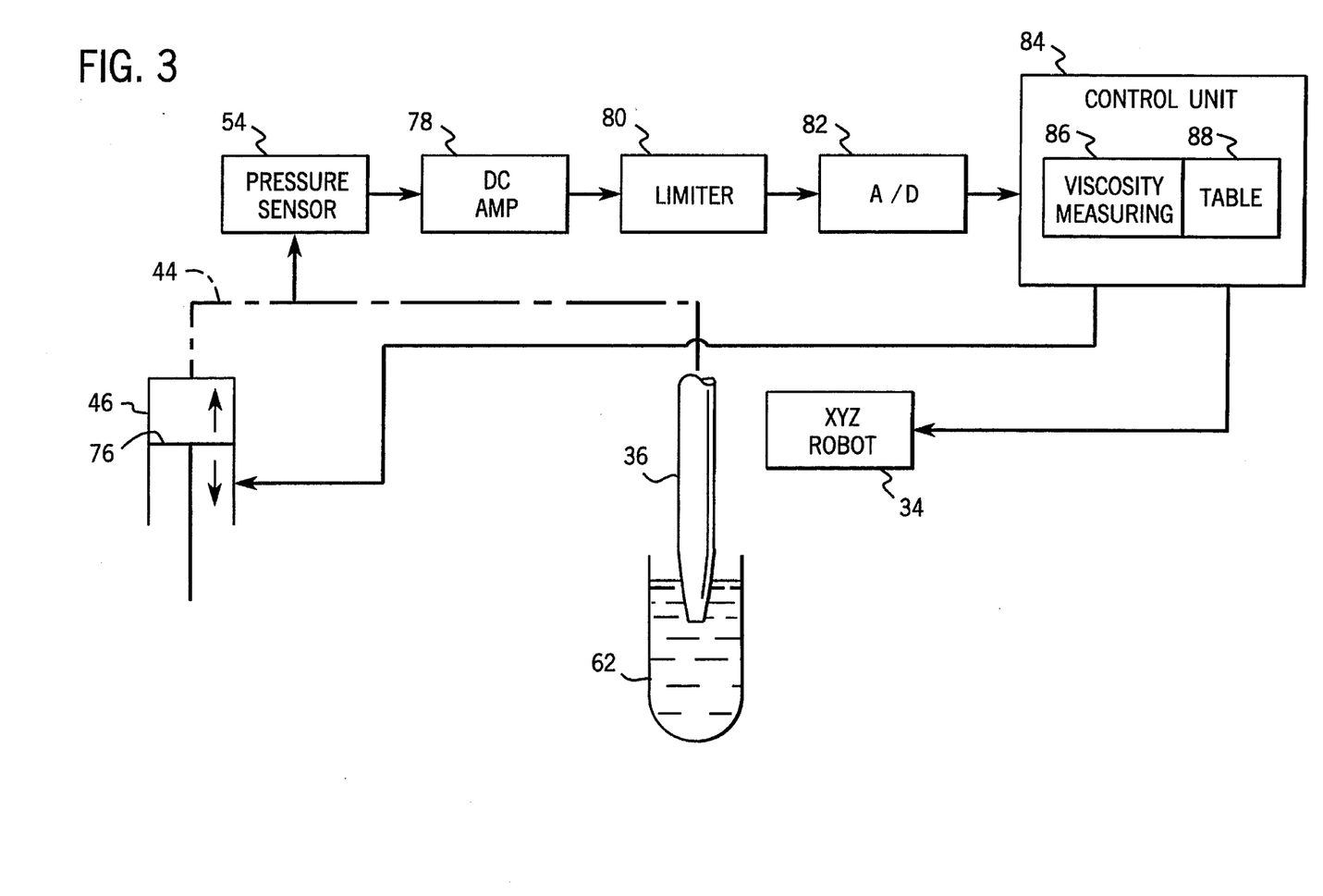
FIG. 3 is a block diagram of the pipetting apparatus of FIG. 1.

FIG. 3 is a block diagram of the apparatus of the embodiment according to the present invention. By moving a piston 76 up and down, inside volume of the syringe 46 varies, so that an aspirating pressure or a dispensing pressure is transmitted to the nozzle tip 36 of the nozzle 32 via the air hose 44 to perform the aspiration or dispensation of the blood sample. The internal pressure of the air hose 44 is detected by the pressure sensor 54, a detected signal outputted from the pressure sensor 54 is amplified by a DC amplifier 78 and is then fed to an analog-digital converter 82 via a limiter circuit 80. The limiter circuit 80 functions as a protection circuit for suppressing any excessive input. The analog-digital converter 82 converts the sensor signal into a digital signal and feeds the digital signal to a control unit 84.

The control unit 84 includes a computer, for example, for controlling the inside volume of the syringe 46, and the XYZ robot 34, etc. In this embodiment, the control unit 84 also includes a viscosity measuring unit 86 and a table 88. The details of the viscosity measuring unit 86 and the table 88 will be below.

Embodiments of the pipetting method according to the present invention, which is preferably used in the above-mentioned apparatus will now be described below.

Figure 4:
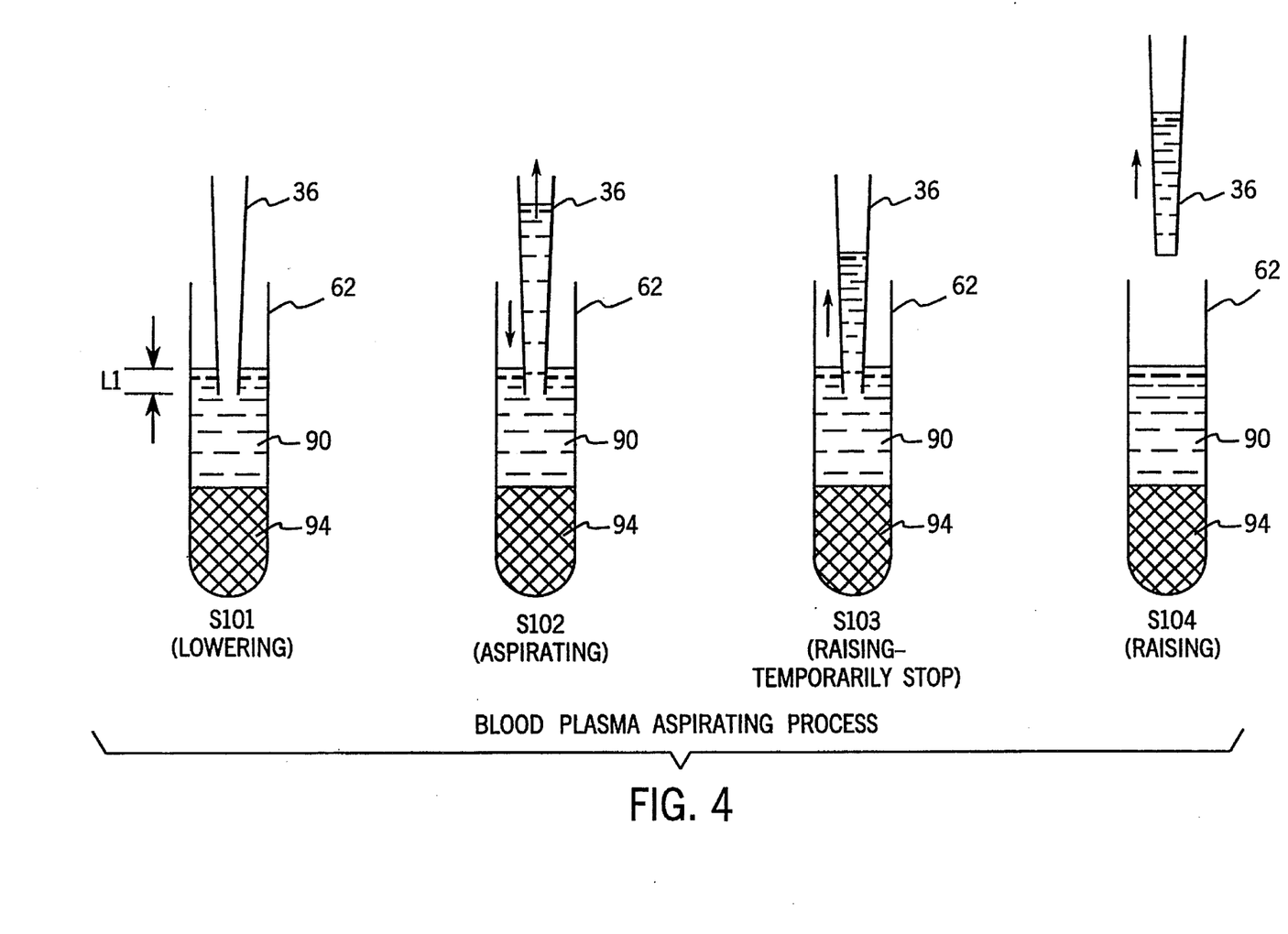
FIG. 4 is an explanatory view showing steps, in which blood plasma is aspirated into the nozzle during a process of pipetting blood plasma.
Figure 5:
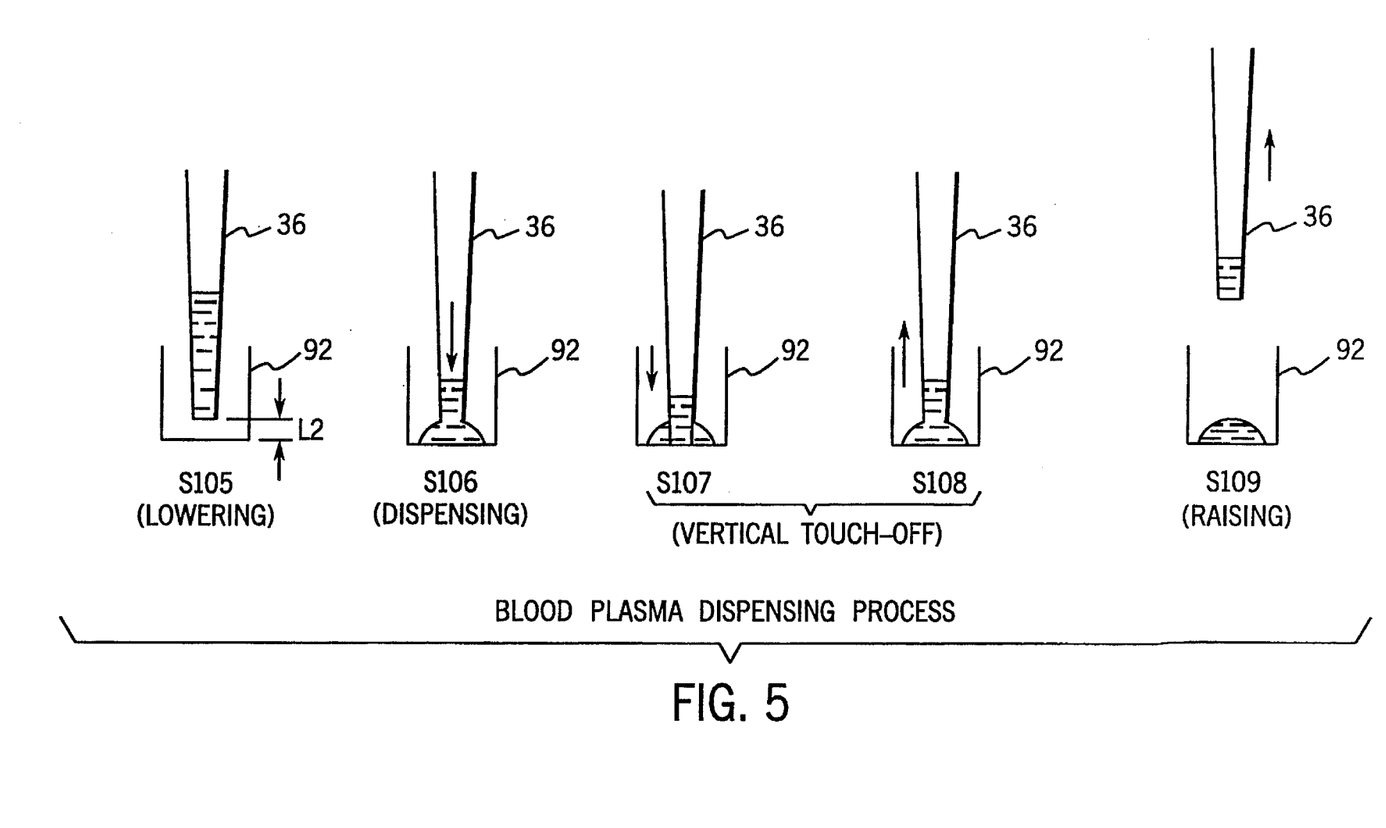
FIG. 5 is an explanatory view showing steps, in which the blood plasma is dispensed from the nozzle during a process of pipetting the blood plasma.

FIGS. 4 and 5 show a blood plasma pipetting process. FIG. 4 shows a blood plasma component aspirating process, and FIG. 5 shows a blood plasma component dispensing process.

In FIG. 4, at step 101, the nozzle tip 36 is lowered from the upper side of the test tube 62 and is stopped so that the distal end of the nozzle tip 36 is inserted into the blood plasma component 90 to be positioned at a predetermined distance L1 downward from a blood surface. L1 is preferably 2 to 3 mm. If the distal end of the nozzle tip 36 is inserted too deeply into the blood plasma component 90, the two components once separated by centrifugation are likely to be mixed again with each other.

When the nozzle tip 36 is lowered, the liquid surface is detected. This liquid surface detection is performed by monitoring the internal pressure of the hose 44 by the pressure sensor 54. When the internal pressure of the hose 44 is changed sharply, the control unit 84 detects that the distal end of the nozzle tip 36 has reached the liquid surface.

At step 102, the blood plasma component 90 is aspirated. Specifically, the piston 76 is pulled downwardly to increase the inside volume of the syringe 46, whereby the blood plasma is aspirated into the nozzle tip 36. For example, about 30 to 300 μl of the blood plasma 90 is aspirated. As described in detail below, this aspirated blood plasma component includes a small volume of blood plasma component to be used for a plasma coating. Preferably, the volume of blood plasma component to be aspirated should be determined by taking account of the volume of blood plasma component that finally would attach onto an inner surface of the nozzle tip 36 and would not be dispensed from the nozzle tip 36.

At step 103, the nozzle tip 36 is raised and stopped temporarily just before the distal end of the nozzle tip 36 leaves from the liquid surface of the blood plasma component 90. After a lapse of, for example, about 0.25 sec., the nozzle tip 36 is raised again at step 104. The reason why the step 103 is needed in this process is that the blood plasma component attaching onto an outer surface of the nozzle tip 36 is returned into the test tube 62, as much as possible thereby improving the precision of the pipetting. Next to step 104, step 105 of FIG. 5 is executed.

In the blood plasma dispensing process shown in FIG. 5, at step 105, the nozzle tip 36 is lowered into a predetermined well 92 and is stopped so that the distal end of the nozzle tip 36 is positioned at a distance L2 off the bottom of the well 92. In this case, L2 is preferably about 2 mm. If the blood plasma component is dispensed from a too high position, it would become a drop, so that it is difficult to transfer the blood plasma component into the well 92 quickly. Further, if the distal end of the nozzle tip 36 comes into contact with the bottom of the well 92, it becomes very difficult to dispense the blood plasma component.

For these reasons as stated in the above, preferable distance L2 is about 2 mm in view of the property of the liquid to be dispensed.

At step 106, a part (predetermined volume) of the blood plasma component existing in the nozzle tip 36 is dispensed.

At step 107, the nozzle tip 36 is lowered until its distal end comes into slight contact with the bottom of the well 92. The contact condition can be monitored by the limit switch 40. At step 108, the nozzle tip 36 is raised. Namely, in step 107 and step 108, a so-called vertical touch-off system is employed, so that the blood plasma component attaching onto the inner surface of the nozzle tip 36 can be dispensed quickly.

At step 109, the nozzle tip 36 is raised and the same dispensing steps (S105–S109) are repeated with respect to other wells. Finally, a predetermined volume of blood plasma component remains in the nozzle tip 36, as shown at step 109 in FIG. 5. This predetermined volume is preferably 15 to 20 μl. The final step 109 of the blood plasma dispensing process shown in FIG. 5 corresponds to a coating preparing step, in which a small volume of blood plasma component remains in the nozzle tip 36 for the purpose of plasma coating.

Figure 6:
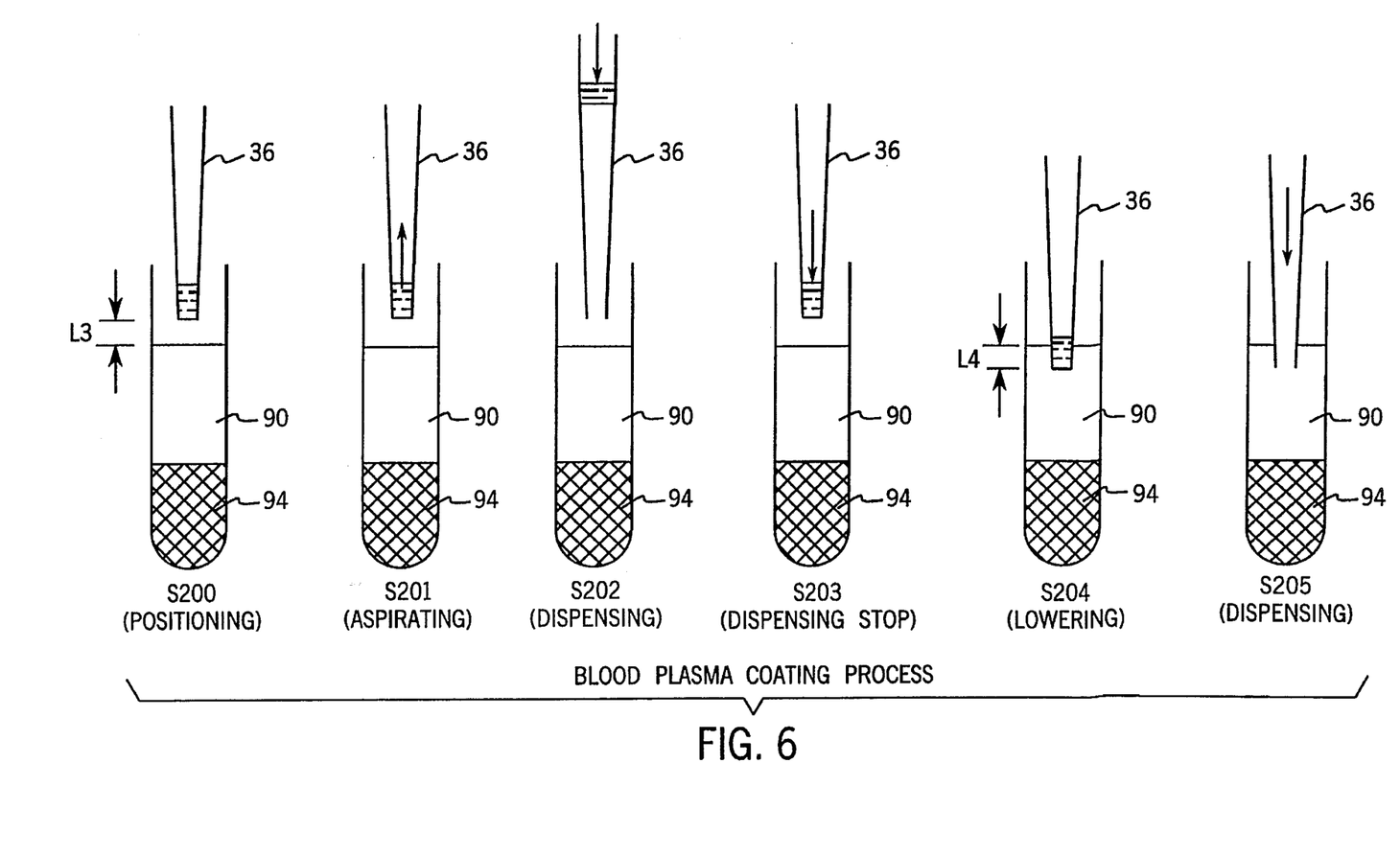
FIG. 6 is an explanatory view showing steps, in which the inner surface of the nozzle is coated with the blood plasma during a process of pipetting red blood cells.
Figure 7:
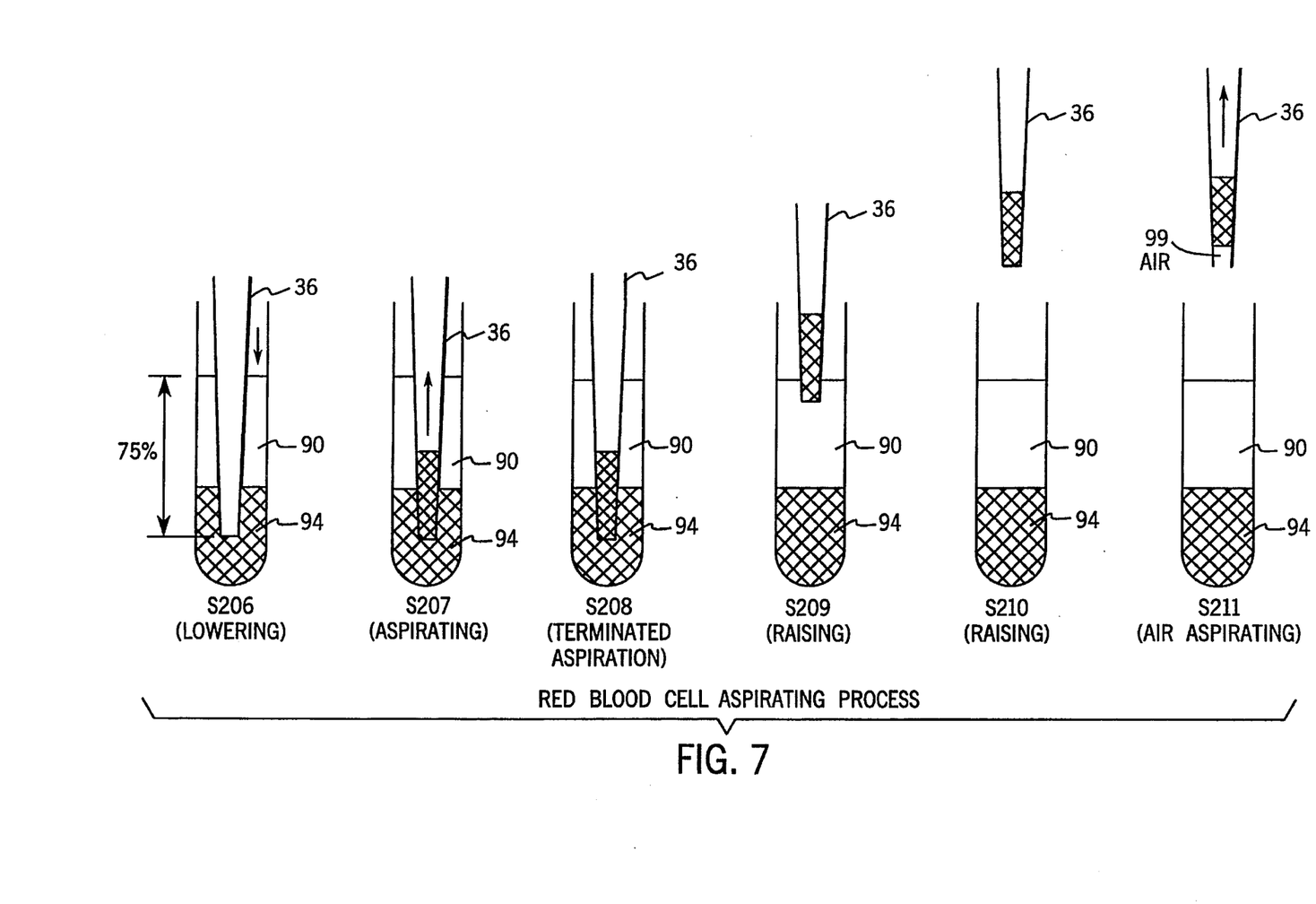
FIG. 7 is an explanatory view showing steps, in which red blood cells are aspirated into the nozzle during the process of pipetting the red blood cells.
Figure 8:
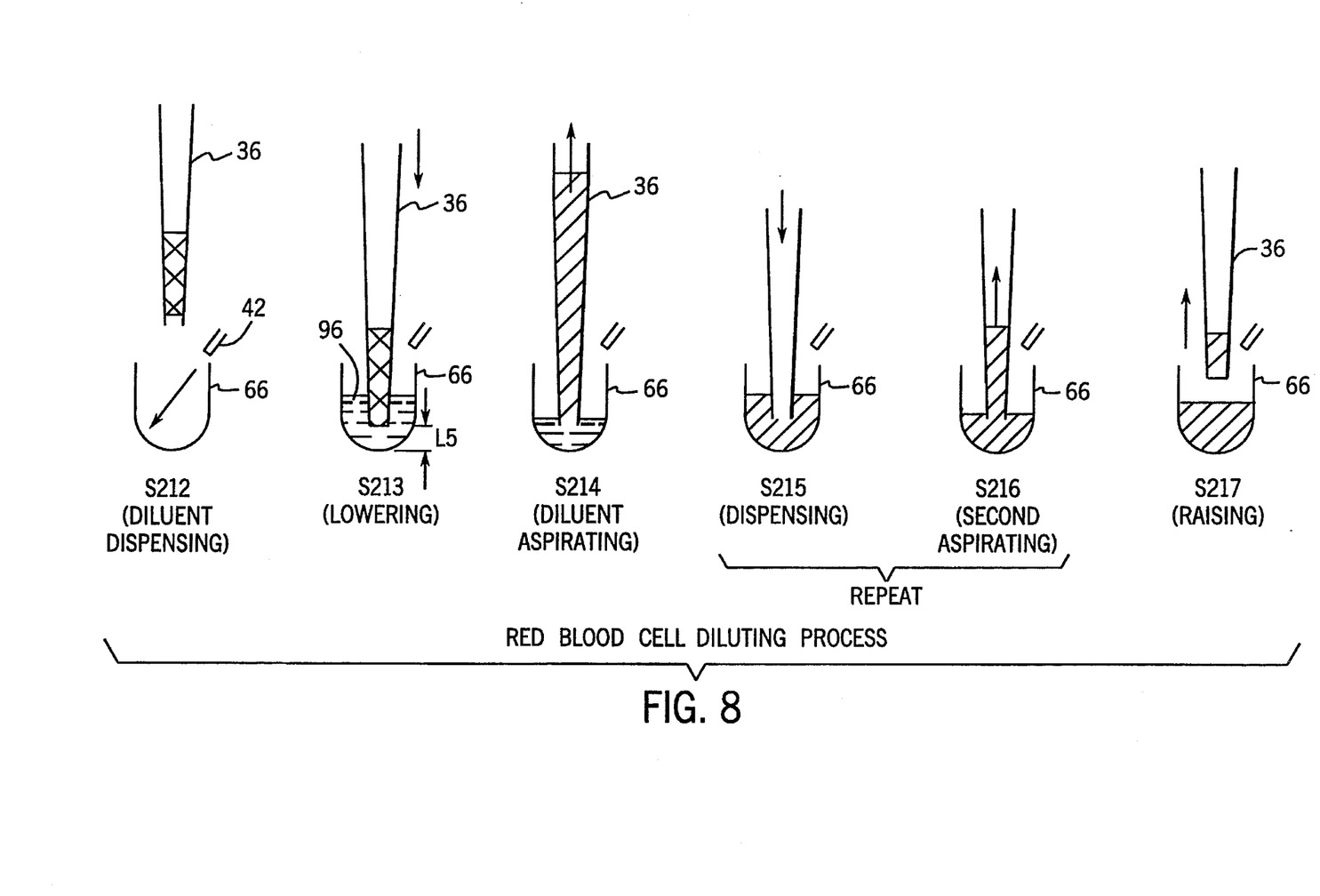
FIG. 8 is an explanatory view showing steps, in which the red blood cells are diluted during the process of pipetting the red blood cells.
Figure 9:
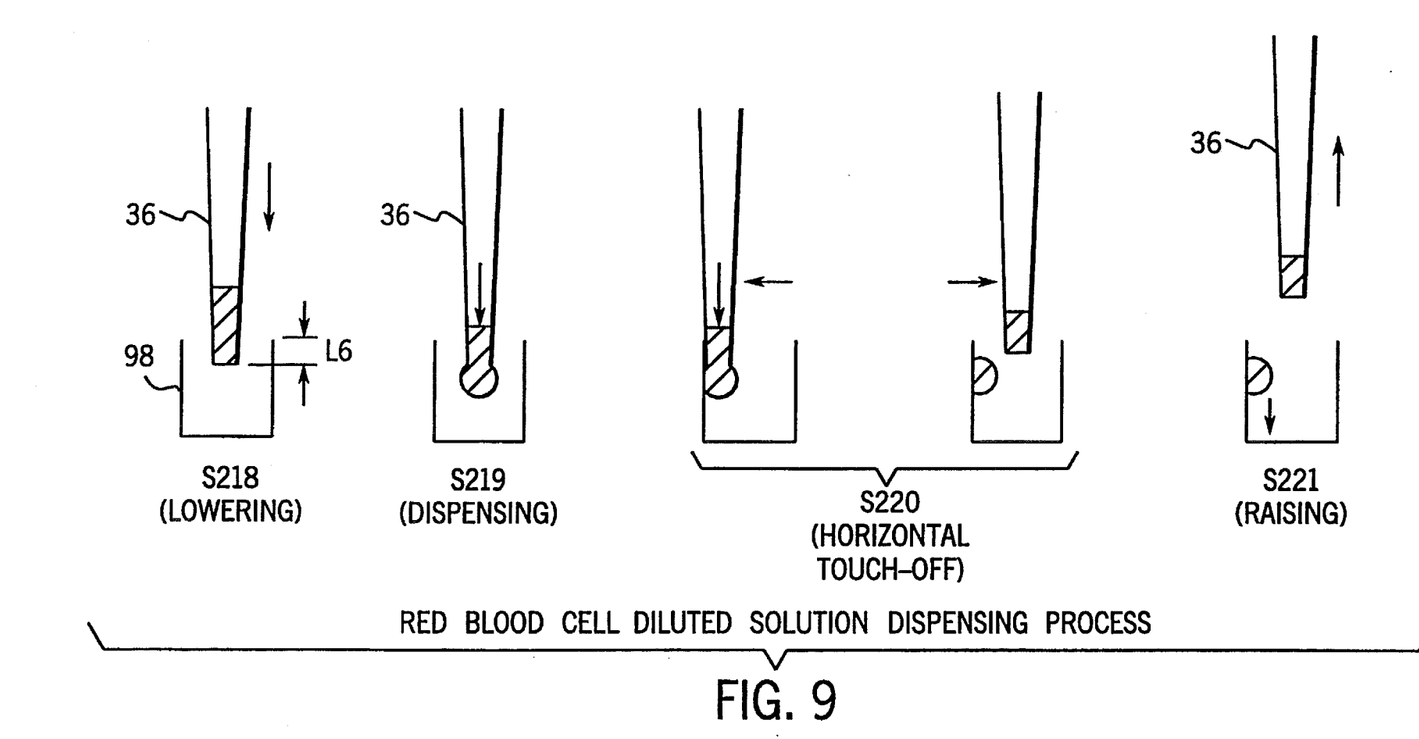
FIG. 9 is an explanatory view showing steps, in which a red blood cell diluent is dispensed from the nozzle during the process of pipetting the red blood cells.

FIGS. 6 through 9 show the red blood cell pipetting process, which generally comprises the following four processes including a blood plasma coating process of FIG. 6; a red blood cell aspirating process of FIG. 7; a red blood cell diluting process of FIG. 8; and a red blood cell diluted solution dispensing process of FIG. 9.

Firstly, the blood plasma coating process will now be described with reference to FIG. 6. After step 109 of FIG. 5, step 200 of FIG. 6 is executed. Namely, by the XYZ robot 34, the nozzle tip 36 is positioned above the test tube 62 from which the blood plasma component has been aspirated at step 102. Specifically, the nozzle tip 36 is positioned so that its distal end is inserted slightly (to be positioned at a distance L3 off the blood surface) into the upper opening of the test tube 62. The above position would prevent the blood plasma coating from scattering over other blood samples and contaminating them, thus improving the reliability of the apparatus. L3 at step 200 is preferably 5 mm.

In the method of this embodiment, pipetting operation is performed continuously by using the same nozzle tip 36 throughout the blood plasma pipetting process and the red blood cell pipetting process. Alternatively, when these two steps processes changeover, the nozzle tip 36 may be exchanged with a new one. In such a case, it is necessary to provide a blood plasma component coating step as a pre-processing step before step 200.

At step 201, the blood plasma component used for the coating which remains in the nozzle tip 36 is aspirated (raised) again at least to such an extent that the red blood cell component to be subsequently aspirated reaches. In more detail, the inner surface of tip 36 is coated to such an extent that the red blood cell component diluted later, i.e., the diluted solution of red blood cells reaches.

At step 202, the blood plasma component for the coating is dispensed (lowered), and the dispensation is stopped when the plasma component reaches the distal end of the nozzle tip 36 as shown at step 203 of FIG. 6.

In this embodiment, the coating is accomplished by moving the blood plasma component up and down only one time as shown at step 201 and step 202. Alternatively, the blood plasma component may be moved up and down two or more times, if necessary. However, it is confirmed that moving up and down one time is sufficient for the coating.

At step 204, the nozzle tip 36 is lowered and stopped when its distal end is inserted into the blood plasma component 90 to be positioned at a distance L4 downward from the blood surface. L4 is preferably 2 to 3 mm. At step 205, the remaining blood plasma component used for the coating is returned into the test tube 62. Thus, in order to use a valuable blood sample without wasting it, the blood plasma component for coating is returned into the test tube 62. Although only a small volume of blood plasma component is used for the coating in this embodiment, a large volume of blood plasma component may be used for the coating. If a large volume of blood plasma component is used, it is necessary to aspirate an unnecessarily large volume of blood plasma component at step 102. Further, in step 205, there is a risk that the blood plasma component is mixed with the red blood cell component when returning such large volume of blood plasma component into the tube. Consequently, it is preferable that the coating should be made with a small volume of blood plasma component.

After step 205, step 206 of FIG. 7 is executed. At step 206, the nozzle tip 36 is further lowered, so that its distal end is inserted into the red blood cell component 94. At that time, it is preferable that the distal end of the nozzle tip 36 is located at a position of about 75% downward from the surface of the blood plasma component, where the whole blood sample is 100%. If the nozzle tip 36 is inserted into the blood plasma component too deeply, a large volume of red blood cell component 94 attaches onto the outer surface of the nozzle tip 36. On the other hand, if the nozzle tip 36 is inserted into the blood plasma component too shallowly, it is difficult to aspirate the red blood cell component surely.

At step 207, the red blood cell component 94 is aspirated. In this embodiment, for example, 80 μl of red blood cell component 94 is aspirated.

However, the red blood cell component 94 is a high viscosity liquid or a gel substance, so that considerable pressure and time are needed to aspirate such red blood cell component via the smaller orifice of the distal end of the nozzle tip 36. In this embodiment, the following two ways are used to improve the quickness of aspiration to a maximum extent. In the first way, the inner surface of the nozzle tip 36 is coated with the blood plasma component in order to reduce the frictional resistance of the inner surface of the nozzle tip 36 as much as possible, thus ensuring a smooth aspiration of the red blood cell component.

In the second way, an excessively large volume of red blood cell component is aspirated temporarily.

Specifically, the piston 76 of the syringe 46 is drawn to a maximum extent, and thereafter the internal pressure of the air hose 44 is monitored by the pressure sensor 54. When the internal pressure becomes equal to a predetermined value α, the piston 76 is returned, so that only a desired volume of red blood cell component is finally aspirated into the nozzle tip 36. In more detail, since a high viscosity solution such as red blood cell component cannot be aspirated so as to quickly follow the moving amount of the syringe 46. Therefore, the maximum aspiration force is applied to the nozzle 36, at an initial aspiration stage, and the moving amount of the syringe 46 is returned to a proper value just before a desired volume of red blood cell component is aspirated, thereby obtaining a predetermined volume of aspirated red blood cell component of which volume is to be determined by the moving amount of the syringe 46. At step 208, when a detection value of the pressure sensor 54 becomes substantially equal to an atmospheric pressure, the termination of aspiration is confirmed. Strictly, since the red blood cell component is aspirated into the nozzle tip 36, the internal pressure of the air hose 44 has a tendency to become lower than the atmospheric pressure. Finally, at step 208, for example, 80 μl of the red blood cell component is aspirated into the nozzle tip 36.

In this embodiment, the aforementioned aspirating operation is controlled by a control means 84 in FIG. 3. In the control means 84, a memory (not shown) for storing a predetermined pressure α shown in FIG. 13 is incorporated, where the predetermined pressure α can be obtained depending on the characteristics of the pump by ah experimental test. Further, in the embodiment of the present invention, a timer for measuring the waiting time after the lapse of the pump moving time is also provided. The timer causes an alarm, when the value of the timer exceeds a predetermined limit value. For example, when the nozzle 36 is plugged, the timer gives a warning.

In the embodiment of the present invention, the aspiration control of the red blood cell is performed as described in the above. The aforementioned aspiration control is also suitable for the blood plasma component.

At step 209, the nozzle tip 36 is raised slowly in order to keep the two blood components stable in a separated state and in order to avoid causing any turbulent flow. Near the liquid surface of the blood plasma component 90, the nozzle tip 36 is temporarily stopped from raising as shown in step 209, and thereafter the nozzle tip 36 is raised again at step 210.

At step 211, for example, about 10 μl of air is aspirated to provide an air cap 99 at the distal end of the nozzle tip 36. This enables to completely take in the nozzle tip 36 the red blood cell component attaching to an edge of the distal end of the nozzle tip 36, and to prevent the red blood cell component from dropping from the nozzle tip 36.

After step 211, step 212 of FIG. 8 is executed. In the step 212, the nozzle tip 36 is conveyed to an upper position above the diluting container 66, at which a predetermined volume of diluent is dispensed into the diluting container 66 through the diluent pipette 42. At step 213, the nozzle tip 36 is lowered from the upper position, so that its distal end is positioned in the diluent 96 at a predetermined distance L5 off the bottom of the diluting container 66. L5 is preferably 2 mm. A physiological salt solution can .be used for the diluent.

At step 214, the diluent 96 is aspirated into the nozzle tip 36. In the conventional method, the red blood cell component was dispensed to be mixed and diluted with the diluent. However, in this embodiment, in view of the facts that the red blood cell component is a high viscosity and dispensation thereof is relatively difficult, the diluent which is easy to be aspirated is previously aspirated, and then the diluent is mixed with the red blood cell component step by step.

At step 215, the mixed solution is dispensed from the nozzle tip 36 into the diluting container 66. At that time, since the red blood cell component is previously diluted by the diluent to a certain degree, the mixed solution can be dispensed extremely easily, as compared with the dispensation of a pure red blood cell component. At step 216, the mixed solution, i.e., the diluted solution of red blood cell is aspirated. In this embodiment, step 215 and step 216 are repeated about five times. During the successive steps from step 214, the aspiration or dispensation is initially performed slowly, depending on the viscosity of the substance to be aspirated or dispensed, and thereafter progressively more quickly. At step 214, since the inner surface of the nozzle tip 36 has been previously coated with the blood plasma component, the diluent can be aspirated into the nozzle tip 36 more smoothly than the case in which the inner surface of the nozzle tip 36 is not coated with the blood plasma component.

At step 217, the nozzle tip 36 is stopped temporarily from being raised when its distal end reaches near the liquid surface, and then the nozzle tip 36 is raised again.

A process of dispensing the diluted solution of the red blood cell solution will now be described.

After step 217, step 218 of FIG. 9 is executed. The nozzle tip 36 is conveyed to a predetermined well 98 on the microplate by the XYZ robot. The nozzle tip 36 is lowered, so that its distal end is positioned in the well 98 at a predetermined distance L6 downward from the upper opening of the diluting container 66, as shown at step 218. L6 is preferably about 3 mm. Though there is not shown in the drawings, a predetermined volume of reagent has been previously pipetting into the respective wells 98.

At step 219, a predetermined volume of diluted solution of red blood cell component in the nozzle tip 36 is dispensed, and then a drop of the diluted solution formed at the distal end of the nozzle tip 36 is attached onto the inner surface of the well 98 at step 220. Namely at step 220, by using the horizontal touch-off system, the diluted solution of red blood cell component is dispensed, without bringing the distal end of the nozzle tip 36 into direct contact with the reagent in the lower portion of the well, thereby preventing contamination from being caused.

At step 221, the nozzle tip 36 is raised and then moved to a next well, and thereafter the steps from step 218 to step 221 are repeatedly executed.

In this embodiment, after the blood plasma pipetting process and the red blood cell pipetting process have been executed for a specific blood sample, the nozzle tip 36 is exchanged with a new one. By using this new nozzle tip, the blood plasma pipetting process and the red blood cell pipetting process are executed in the same way for other blood samples.

The viscosity measuring unit 86 of FIG. 3 will now be described hereinbelow. The viscosity of the red-blood cell component is valuable information for diagnosing an illness and is also a valuable material for determining an aspiration pressure to be set when a blood sample is pipetted. In the conventional apparatus, there is not provided any viscosity measuring unit, and the viscosity of a blood sample is measured by a separate measuring instrument. Therefore, after having been subjected to the viscosity measurement, the blood sample has been disused. Further, the viscosity measurement takes a long time and needs a complex operation.

In the apparatus of the present invention, since the control unit 84 is equipped with the viscosity measuring unit 86, it is possible to measure the viscosity of the blood sample while the blood sample being pipetted.

In various liquids having different viscosities, there is a close relationship between the viscosity of each liquid and the time required from a point of time when a predetermined pressure is produced as an initial aspiration pressure for aspirating the liquid to a point of time when the aspiration pressure reaches a certain pressure value. It was confirmed in a simulation that there is a proportional relation ship therebetween.

In a table 88, there is stored data which represents a relationship between the viscosity of the liquid to be aspirated and the time required from a point of time when the liquid begins to be aspirated under a certain initial aspiration pressure to a point of time when the pressure which returns gradually to an atmospheric pressure reaches a specifically set pressure value.

Specifically, when aspirating the blood sample into the nozzle tip 36, the internal pressure of the air tube 44 is monitored by the pressure sensor 54, and the viscosity measuring unit 86 measures the time required from a point of time when the piston 76 is drawn to give the initial aspiration pressure, to a point of time when the internal pressure of the air tube 44 reaches a predetermined value. The viscosity measuring unit 86 also obtains a viscosity of the blood sample by comparing the measured time with the table 88. The obtained viscosity is indicated on a display unit (not shown), and this result is utilized for controlling the syringe 46 by the control unit 84.

According to the viscosity measuring unit 86 described above, there are advantages as follows. Since the viscosity can be measured simultaneously with the aspiration of the blood sample, the unit 86 requires no additional time for measuring the viscosity, and realizes a very simple viscosity measurement. Further, it is unnecessary to prepare an additional blood sample only for viscosity measurement.

ADVANTAGEOUS EFFECTS OF THE INVENTION

As aforementioned, according to the present invention, at a starting time of the aspiration of the liquid sample, the aspirating force which is greater than that by a conventional method can be produced. When the pressure of the aspirating system becomes equal to the predetermined value, the moving amount of the piston is returned to such a degree that only a necessary aspiration volume of the liquid sample can be aspirated, and finally, only the necessary aspiration volume can be aspirated. Therefore, when the liquid sample having high viscosity is aspirated, it can be aspirated in a short time. For example, in the pipetting apparatus, there is advantages of improving a pipetting operation and pipetting ability.

EXPLANATION OF REFERENCES NUMERALS 30 pipetting apparatus
32 nozzle
34 XYZ robot
35 nozzle base
36 disposable tip
54 pressure sensor
84 control unit
86 viscosity measuring unit
90 blood plasma component
94 red blood cell component

What is claimed is:

1. A liquid aspirating method for use with an aspirating apparatus which includes a nozzle tip for aspirating a liquid sample, an aspirating pump having a piston and a syringe connected with said nozzle tip, and a pressure sensor for monitoring a pressure in an aspirating system, in which an aspirating volume of said liquid sample into the nozzle tip is determined on the basis of a moving amount of said piston, wherein said method comprising the steps of:

(a) moving said piston to aspirate a liquid sample more than a necessary aspirating volume into the nozzle tip, when starting the aspiration; and (b) moving the piston to aspirate only the necessary aspirating volume into the nozzle tip, when the pressure in the aspirating system becomes equal to a predetermined pressure; thereby aspirating only the necessary volume of the liquid sample into the nozzle tip.

* * * * *